United States Patent [19]

Steiner et al.

[11] Patent Number: 5,616,705
[45] Date of Patent: Apr. 1, 1997

[54] N-SUBSTITUTED AZABICYCLOHEPTANE DERIVATIVES, THEIR PREPARATION AND USE

[75] Inventors: Gerd Steiner, Kirchheim; Rainer Munschauer, Neustadt; Liliane Unger, Ludwigshafen; Hans-Jürgen Teschendorf, Dudenhofen; Thomas Höger, Edingen-Neckarhausen, all of Germany

[73] Assignee: BASF Aktiengesellschaft, Ludwigshafen, Germany

[21] Appl. No.: 632,398

[22] PCT Filed: Nov. 26, 1994

[86] PCT No.: PCT/EP94/03910

§ 371 Date: Apr. 19, 1996

§ 102(e) Date: Apr. 19, 1996

[87] PCT Pub. No.: WO95/15312

PCT Pub. Date: Jun. 8, 1995

[30] Foreign Application Priority Data

Dec. 4, 1993 [DE] Germany .......................... 43 41 402.8

[51] Int. Cl.$^6$ .................................................. C07D 209/52

[52] U.S. Cl. ..................... 544/105; 544/230; 544/318; 544/349; 546/183; 546/221; 548/208; 548/230; 548/362.5; 548/411; 548/434; 548/454

[58] Field of Search .................................. 544/105, 230, 544/318, 349; 546/183, 221; 548/208, 230, 362.5, 411, 434, 454

[56] References Cited

FOREIGN PATENT DOCUMENTS 4219973  12/1993  Germany .
9218480  10/1992  WIPO .
9515312  6/1995   WIPO .

Primary Examiner—Johann Richter
Assistant Examiner—Jane C. Oswecki
Attorney, Agent, or Firm—Keil & Weinkauf

[57] ABSTRACT

Compounds of the formula I

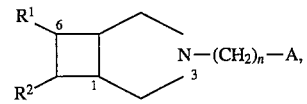

where the substituents have the meanings given in the description, and their preparation are described. The novel compounds are suitable for the control of diseases.

2 Claims, No Drawings

N-SUBSTITUTED AZABICYCLOHEPTANE DERIVATIVES, THEIR PREPARATION AND USE

This application is a 371 of PCT/EP94/03910 Nov. 26, 1994.

The invention relates to novel N-substituted azabicycloheptane derivatives, their preparation and use for preparing pharmaceuticals.

It has been disclosed that basically substituted butyrophenone derivatives or benzamide derivatives have neuroleptic or cerebro-protective activity (U.S. Pat. No. 4,605,655, EP 410 114, DE 12 89 845, EP 400 661, DE 29 41 880, EP 190 472, DE 42 19 973).

The observed high affinities to dopamine and serotonin receptor subtypes appear to play a particular role in this context. It has now been found that N-substituted 3-azabicyclo[3.2.0]-heptane derivatives of the formula I $$\begin{array}{c} R^1 \\ R^2 \end{array} \overset{6}{\underset{1}{\square}} \rangle N-(CH_2)_n-A, \qquad I$$

where $R^1$ is a phenyl or thienyl group which is unsubstituted or mono- or disubstituted by halogen atoms or $C_1$–$C_4$-alkyl, trifluoromethyl, hydroxyl, $C_1$–$C_4$-alkoxy, amino, monomethylamino, dimethylamino, cyano or nitro groups, $R^2$ is a hydrogen atom or a phenyl group which is unsubstituted or substituted by halogen, methoxy, hydroxyl or amino, n is the number 1, 2, 3 or 4, A is a hydrogen atom or one of the radicals $R^3$ is a hydrogen atom or a hydroxyl radical, $R^4$ is a hydrogen atom or $R^3$ and $R^4$ together are an oxygen atom, $R^5$ is a thienyl or naphthyl group which is unsubstituted or substituted by fluorine or chlorine, $R^6$ is a hydrogen atom or a methyl group, and $R^7$ is a phenyl group which is disubstituted by fluorine, chlorine, hydroxyl or methoxy or monosubstituted by amino, $C_{1-4}$-alkylamino or di-$C_{1-4}$-alkylamino or a thienyl, naphthyl, benzofuryl, benzothienyl, indolyl, N-methylindolyl or indenyl group which is unsubstituted or substituted by fluorine, chlorine or nitro or a $C_3$- to $C_6$-cycloalkyl group, $R^8$ is hydrogen, fluorine, chlorine, $C_{1-4}$-alkyl, methoxy or amino, $R^9$ is hydrogen or a methyl group and $R^{10}$ is hydrogen or a methyl group or $R^9$ and $R^{10}$, together with the ring C atom, are a spirocyclopropane ring, $R^{11}$ is a phenyl or benzyl radical which is unsubstituted or substituted by fluorine or chlorine, or a cyano group, and their salts with physiologically tolerable acids, have useful pharmacological properties.

In the formula I, the substituents $R^1$ to $R^{10}$ and n preferably have the following meanings:

$R^1$: phenyl and thienyl, unsubstituted or substituted by fluorine, chlorine, iodine, methoxy, trifluoromethyl or nitro, $R^2$: hydrogen, n: 1 or 2, R³: hydrogen,
R⁴: hydrogen,
R⁵: 1-naphthyl,
R⁶: hydrogen,
R7: o-aminophenyl, o-N-methylaminophenyl, 5-chlorothien-l-yl, 1-naphthyl, 3-indenyl, cyclohexyl, 3-chloro-l-benzothien-2-yl,
R⁸: hydrogen,
R⁹: hydrogen, methyl,
R¹⁰: hydrogen, methyl,
R¹¹: phenyl.

The compounds of the formula I according to the invention can be prepared by reacting a compound of the formula II

$$Nu-(CH_2)_n-A \qquad (II),$$

where A and n have the meanings given and Nu is a nucleofugic leaving group, with a 3-azabicyclo[3.2.0]heptane derivative of the formula III

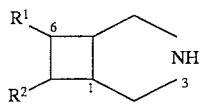

where
- R¹ is a phenyl or thienyl group which is unsubstituted, mono- or disubstituted by halogen atoms or $C_4-C_4$-alkyl, trifluoromethyl, hydroxyl, $C_1-C_4$-alkoxy, amino, monomethylamino, dimethylamino, cyano or nitro groups and
- R² is a hydrogen atom or a phenyl group which is unsubstituted or substituted by halogen, methoxy, hydroxyl or amino, and if desired converting the compounds thus obtained into their acid addition salts with physiologically tolerable acids.

Suitable nucleofugic leaving groups for Nu are preferably halogen atoms, in particular bromine or chlorine.

The reaction is expediently carried out in the presence of an inert base, such as triethylamine or potassium carbonate, as acid acceptor in an inert solvent, such as a cyclic saturated ether, in particular tetrahydrofuran or dioxane, or a benzene hydrocarbon, such as toluene or xylene.

The reaction is in general carried out at from 20° to 150° C., and is in general complete within from 1 to 10 hours.

The compounds of the formula I according to the invention can either be recrystallized by recrystallization from the customary organic solvents, preferably from a lower alcohol, such as ethanol, or purified by column chromatography.

Racemates can be resolved into the enantiomers in a simple manner by classical cleavage using optically active carboxylic acids, eg. tartaric acid derivatives, in an inert solvent, eg. lower alcohols.

The free 3-azabicyclo[3.2.0]heptane derivatives of the formula I can be converted to the acid addition salt of a pharmacologically tolerable acid in a customary manner, preferably by treating a solution with an equivalent of the corresponding acid. Pharmaceutically tolerable acids are, for example, hydrochloric acid, phosphoric acid, sulfuric acid, methanesulfonic acid, sulfamic acid, maleic acid, fumaric acid, oxalic acid, tartaric acid or citric acid.

The compounds according to the invention have useful pharmacological properties. They can be used as neuroleptics (in particular atypical), antidepressants, sedatives, hypnotics, CNS protectants or muscle relaxants. Several of the active qualities can occur in combination in one compound according to the invention. Demonstration of the pharmacological action is carried out both in vivo and in vitro, substance characterization in particular being possible as a result of the in some cases very high and selective affinity to receptor subtypes, eg. dopamine $D_1$, $D_2$, $D_3$ and especially $D_4$ receptors; serotonin 1A, 1D and 2 receptors; alpha 1 and 2 receptors; histamine 1 and muscarine receptors.

The following methods were used for the in vivo characterization of the novel substances:

a) Effect on Orientation Motility

In a new environment, mice show increased exploratory behavior which is manifested by increased motor activity. This motor activity is measured in light barrier cages for 0–30 min after the animals (female NMRI mice) have been placed in the cages.

ED50: dose which reduces the motor activity by 50% in comparison with placebo-treated controls.

b) Apomorphine Antagonism

Female NMRI mice receive 1.21 mg/kg of apomorphine s.c. At this dose, apomorphine leads to motor activation which is manifested by continuous climbing when the animals are kept in wire mesh cages. The climbing is assessed using a score (every 2 min for 30 min):

0: animal has four paws on the floor
1: animal has two paws on the wire
2: animal has four paws on the wire (is climbing).

The climbing behavior can be inhibited by pretreatment with antipsychotics.

ED50: dose which inhibits the climbing activity of the animals by 50% in comparison with placebo-treated controls.

c) L-5-HTP Antagonism

Female Sprague-Dawley rats receive L-5-HTP in a dose of 316 mg/kg i.p. The animals subsequently develop an excitation syndrome of which the symptoms forepaw treading and
tremor are assessed with the aid of a score (0=not present, 1=moderate, 2=clearly marked) every 10 min in the period from 20 to 60 min after L-5-HTP administration. On average, a score of 17 is achieved after L-5-HTP administration. The test substances are given p.o. 60 min before L-5-HTP. The ED50 is calculated as the dose which on average decreases the control score by 50%.

The methods mentioned are suitable for characterizing substances as antipsychotics. A serotonin-antagonistic effect may be shown by the inhibition of the L-5-HTP syndrome, a type of effect which is characteristic of the atypical neuroleptics.

The novel compounds show a good action in these tests.

The invention accordingly also relates to a therapeutic composition, which contains a compound of the formula I or its pharmacologically tolerable acid addition salt as active compound in addition to customary excipients and diluents, and the use of the novel compounds in the control of diseases.

The compounds according to the invention can be administered in a customary manner orally or parenterally, intravenously or intramuscularly.

The dosage depends on the age, condition and weight of the patient and on the mode of administration. As a rule, the daily dose of active compound is from about 1 to 100 mg/kg of body weight on oral administration and from 0.1 to 10 mg/kg of body weight on parenteral administration.

The novel compounds can be used in conventional solid or liquid pharmaceutical administration forms, eg. as tablets, film tablets, capsules, powders, granules, coated tablets, suppositories, solutions, ointments, creams or sprays. These are prepared in a customary manner. The active compounds can in this case be processed with the customary pharmaceutical auxiliaries such as tablet binders, fillers, preservatives, tablet disintegrants, flow regulators, plasticizers, wetting agents, dispersants, emulsifiers, solvents, release-delaying agents, antioxidants and/or propellant gases (cf. H. Sucker et al.: Pharmazeutische Technologie [Pharmaceutical Technology], Thieme-Verlag, Stuttgart, 1978). The administration forms thus obtained normally contain the active compound in an amount from 1 to 99% by weight.

The substances of the formula II required as starting substances for the synthesis of the novel compounds are known or can be prepared by the methods described in the literature.

The substances of the formula III can be prepared by subjecting an amine of the formula IV

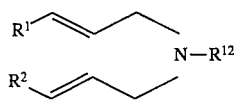    IV where $R^1$ and $R^2$ have the meanings given above and $R^{12}$ is hydrogen, acetyl, benzyl or trifluoroacetyl, photochemically to a 2+2 cycloaddition and then, if appropriate, removing an acyl or benzyl group.

The photoreaction takes place readily in an inert solvent, preferably acetone, at from 20° to 80° C. A particularly highly suitable light source is a mercury high-pressure lamp. It may be advantageous to carry out the photocycloaddition in a quartz apparatus under a nitrogen atmosphere, if appropriate with addition of about 1 mol of hydrochloric acid per mole of amine.

The photocycloaddition in most cases proceeds with high diastereoselectivity to give the bicyclic compounds III having the exo configuration with respect to $R^1$ and $R^2$:

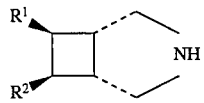

The two enantiomers can be isolated in pure form by resolution of racemate, eg. with optically active tartaric acid derivatives.

Removal of an acyl radical ($R^{12}$) is expediently carried out by hydrolysis according to known methods. The same applies for the removal of the benzyl radical.

The amines of the formula IV are known from the literature or can be prepared by either reacting an aldehyde $R^1$—CHO with vinyl-magnesium chloride to give the allyl alcohol V

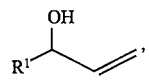    V then rearranging with hydrogen chloride to give the allyl chloride VI

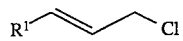    VI and finally reacting with the appropriate allylamine VII

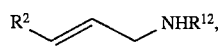    VII or subjecting a cinnamaldehyde VIII

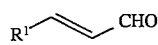    VIII directly to reductive amination with the allylamine VII.

The following examples serve to illustrate the invention:

A) Preparation of the starting materials 1. exo-6-(p-Fluoro)phenyl-3-azabicyclo[3.2.0]heptane 19.4 g (102 mM of N-allyl-N-[3-(4-fluorophenyl)-allyl] amine in 130 ml of acetone were mixed with 130 ml of 10% strength hydrochloric acid and with 600 mg of Michler's ketone and irradiated in a quartz apparatus at room temperature under nitrogen for 55 h using a 150 watt mercury high-pressure lamp. The reaction mixture was then concentrated and the residue was partitioned between methylene chloride and water. The mixture was rendered alkaline with aqueous ammonia solution and the aqueous phase was extracted a further two times with methylene chloride. The combined organic phases were dried with sodium sulfate and concentrated.

Yield 19.3 g (99%), m.p. 165°–166° C. (maleate)

To separate the antipodes, 15.0 g (78.5 mM) of the racemate were mixed with a solution of 31.7 g (78.5 mM) of (–)-di-O-toluoyl-L-tartaric acid in 300 ml of boiling ethanol. The crystals (13.8 g) which precipitated on cooling with stirring were filtered off with suction and washed with ethanol and recrystallized from 200 ml of ethanol with addition of 200 ml of water. Liberation of the base yielded the (+)-antipode (5.5 g) having $[\alpha]_D$=+97.0°

(EtOH, c=0.969).

14.2 g of a salt crystallized from the above mother liquor overnight and was recrystallized (removal of the insoluble component by filtering at boiling heat) from 400 ml of ethanol (concentration to 300 ml). Liberation of the base yielded 4.0 g of the (–)-antipode, $[\alpha]_D$=–96.0°

(EtOH, c=0.940).

The exo-phenyl configurations were confirmed by X-ray structural analysis.

2. exo-6-Phenyl-3-azabicyclo[3.2.0]heptane 50.0 g (28.9 mM) of N-cinnamyl-N-allylamine in 1600 ml of acetone were mixed with 300 ml of 10% strength hydrochloric acid and irradiated in a quartz apparatus at room temperature under nitrogen for 48 h using a 150 watt mercury high-pressure lamp. The reaction mixture was then concentrated and the residue was partitioned between methylene chloride and water. The mixture was rendered alkaline with aqueous ammonia solution and the aqueous phase was reextracted a further two times with methylene chloride. The combined organic phases were dried with sodium sulfate and concentrated.

Yield 49.0 g (98%) of viscous oil, m.p. 177°–178° C. (maleate).

3. exo-6,7-Diphenyl-3-benzyl-3-azabicyclo[3.2.0] heptane 70.0 g (206 mM) of bis(N-cinnamyl)benzylamine in 2500 ml of acetone were mixed with 0.8 g of Michler's ketone and irradiated in a Duran glass apparatus at room temperature under nitrogen for 25 h using a 150 watt mercury high-pressure lamp. The reaction mixture was then concentrated and the residue was partitioned between methylene chloride and water. The mixture was rendered alkaline with aqueous ammonia solution and the aqueous phase was reextracted a further two times with methylene chloride. The combined organic phases were dried with sodium sulfate and concentrated. Purification of the crude product (65.0 g) was carried out by column chromatography (silica gel, eluent toluene, ethanol 98:2). 58.0 g (83%) of product were obtained, m.p. 230°–232° C. (hydrochloride).

4. exo-6,7-Diphenyl-3-azabicyclo[3.2.0]heptane 16.0 g (254 mM) of ammonium formate and 2.0 g of palladium (10% strength) on carbon were added to 12.0 g (35.4 mM) of exo-6,7-diphenyl-3-benzyl-3-azabicyclo [3.2.0]heptane in a mixture of 300 ml of n-propanol and 16 ml of water and the reaction mixture was refluxed for 4 h (evolution of carbon dioxide). After cooling, the catalyst was filtered off with suction and washed with propanol and methylene chloride, and the filtrate was concentrated. The residue was partitioned between methylene chloride and water and rendered alkaline with aqueous ammonia solution, and the aqueous phase was reextracted a further two times with methylene chloride. The combined organic phases were dried with sodium sulfate and concentrated. 8.1 g (92%) of product were obtained, m.p. 140° to 142° C. (maleate).

5. exo-6-Phenyl-3-benzyl-3-azabicyclo[3.2.0]heptane 9.2 g (35.0 mM) of N-cinnamyl-N-allylbenzylamine in 1100 ml of acetone were mixed with 100 mg of Michler's ketone and irradiated in a Duran glass apparatus at room temperature under nitrogen for 5 h using a 150 watt mercury high-pressure lamp. The reaction mixture was then concentrated. Purification of the crude product (9.4 g) was carried out by column chromatography (silica gel, eluent methylene chloride/methanol 98:2). 3.3 g (36%) of product were obtained, m.p.: 126°–128° C. (maleate).

6. 2,2,2-Trifluoro-1-[exo-6-(3-pyridyl)-3-azabicyclo [3.2.0]-hept-3-yl]ethanone 14.0 g (51.8 mM) of N-allyl-2,2,2-trifluoro-N-[3-(3-pyridyl)allyl]acetamide were dissolved in 140 ml of acetone, mixed with 30 ml of 10 % strength aqueous hydrochloric acid and irradiated in a Duran glass apparatus at room temperature under nitrogen for 48 h using a 150 watt mercury high-pressure lamp. The reaction solution was then concentrated, taken up in 150 ml of water and adjusted to pH 8–9 with aqueous ammonia solution. The aqueous phase was extracted twice with tert-butyl methyl ether, and the combined organic phases were dried over sodium sulfate and concentrated. The residue which remained was fractionated by means of column chromatography (silica gel, methylene chloride+2% methanol). 6.2 g (42%) of unchanged N-allyl-2,2,2-trifluoro-N-[3-(3-pyridyl)-allyl]acetamide and 3.7 g (26%) of 2,2,2-trifluoro-1-[exo-6-(3-pyridyl)-3-azabicyclo [3.2.0]hept-3-yl]ethanone were obtained as a dark oil.

7. exo-6-(3-Pyridyl)-3-azabicyclo[3.2.0]heptane 2.5 g of potassium hydroxide pellets were added to a solution of 3.7 g (13.7 mM [sic]) of 2,2,2-trifluoro-1-[exo-6-(3-pyridyl)-3-azabicyclo[3.2.0]hept-3-yl]ethanone in 50 ml of ethanol. The reaction solution was stirred at room temperature for a further 2 h and then poured onto 100 ml of ice-water. The aqueous phase was extracted three times with tert-butyl methyl ether, and the combined organic phases were dried over sodium sulfate and concentrated. Yield 2.3 [lacuna] (96%) of yellow oil, m.p. 202°–205° C. (hydrochloride).

The following substances can be prepared in a similar manner:

8. exo-6-(m-Fluorophenyl)-3-azabicyclo[3.2.0]heptane
9. exo-6-(o-Fluorophenyl)-3-azabicyclo[3.2.0]heptane, m.p. 118°–120° C. (maleate)
10. exo-6-(p-Chlorophenyl)-3-azabicyclo[3.2.0]heptane, m.p. 152°–154° C. (maleate)
11. exo-6-(m-Chlorophenyl)-3-azabicyclo[3.2.0]heptane, m.p. 130°–132° C. (maleate)
12. exo-6-(p-Methoxyphenyl)-3-azabicyclo[3.2.0]heptane
13. exo-6-(m-Methoxyphenyl)-3-azabicyclo[3.2.0]heptane
14. exo-6-(p-Nitrophenyl)-3-azabicyclo[3.2.0]heptane, m.p. 158°–160° C. (maleate)
15. exo-6-(m-Nitrophenyl)-3-azabicyclo[3.2.0]heptane
16. exo-6-(p-Trifluoromethylphenyl)-3-azabicyclo[3.2.0] heptane, m.p. 155°–156° C. (maleate)
17. exo-6-(m-Trifluoromethylphenyl)-3-azabicyclo[3.2-0] heptane
18. exo-6-(3,4-Difluorophenyl)-3-azabicyclo[3.2-0]heptane
19. exo-6-(3,5-Dichlorophenyl)-3-azabicyclo[3.2.0]heptane, m.p. >250° C. (hydrochloride)
20. exo-6-(3,4-Dimethoxyphenyl)-3-azabicyclo[3-2.0]heptane
21. exo-6-(m-Hydroxyphenyl)-3-azabicyclo[3.2-0]heptane
22. exo-6-(p-Hydroxyphenyl)-3-azabicyclo[3.2.0]heptane
23. exo-6-(3,4-Dihydroxyphenyl)-3-azabicyclo[3-2.0]heptane
24. exo-6-(p-Methylphenyl)-3-azabicyclo[3.2.0]heptane
25. exo-6-(m-Methylphenyl)-3-azabicyclo[3-2.0]heptane
26. exo-6-(p-t-Butylphenyl)-3-azabicyclo[3-2-0]heptane, m.p. >255° C. (hydrochloride)
27. exo-6-(m-Aminophenyl)-3-azabicyclo[3.2-0]heptane
28. exo-6-(p-Aminophenyl)-3-azabicyclo[3.2.0]heptane
29. exo-6-(p-Cyanophenyl)-3-azabicyclo[3-2.0]heptane, m.p. 168°–170° C. (maleate)
30. exo-6-Thien-2-yl-3-azabicyclo[3.2.0]heptane, m.p. 180°–182° C. (hydrochloride)
31. exo-6-Thien-3-yl-3-azabicyclo[3.2.0]heptane, m.p. 143°–145° C. (hydrochloride)
32. exo-6-(5-Chlorothien-2-yl)-3-azabicyclo[3-2.0]heptane, m.p. 156°–157° C. (maleate)

Preparation of the final products

Example 1

N-(2-[exo-6-p-Fluorophenyl-3-azabicyclo[3.2.0] heptan-3-yl]-ethyl)benzosulfonamide hydrochloride 3.0 g (15.7 mM) of exo-6-p-fluorophenyl-3-azabicyclo-[3.2.0]heptane in 60 ml of xylene were mixed with 3.5 g (15.7 mM) of N-(2-chloroethyl)benzosulfonamide and with 2.2 g (15.7 mM) of finely pulverized potassium carbonate in addition to 0.5 g of potassium iodide and the mixture was refluxed for 4 h with vigorous stirring.

After cooling, it was concentrated on a rotary evaporator and the residue was partitioned between methylene chloride and water (pH=10).

The aqueous phase was reextracted twice with methylene 2O chloride and the organic phase was then concentrated after washing once with water and drying with sodium sulfate. The crude product (7.6 g) was purified by column chromatography (silica gel, eluent methylene chloride/methanol 98:2). The free base was taken up in 30 ml of ethyl acetate, the insoluble flocks were filtered off and the ether solution was mixed with excess ethereal hydrochloric acid. After stirring for 1 h, 150 ml of ether were added and the mixture was allowed to stand overnight. The solid was then filtered off with suction in the cold and the hydrochloride was washed with a copious amount of ether. 4.1 g (64%) of product were isolated, m.p. 133° to 135° C.

The following can be prepared in a similar manner:
2. N-(2-[exo-6-Phenyl-3-azabicyclo[3.2.0]heptan-3-yl]-ethyl)benzosulfonamide, m.p. 116°–118° C. (hydrochloride).
3. N-(2-[exo-6-p-Fluorophenyl-3-azabicyclo[3.2.0]heptan-3-yl]ethyl)-N-methylbenzosulfonamide, m.p. 63°–65° C. (hydrochloride)
4. N-(2-[exo-6-(5-Chlorothien-2-yl)-3-azabicyclo[3.2.0]heptan-3-yl]ethyl)-4-fluorobenzosulfonamide
5. 3-[exo-6-p-Fluorophenyl-3-azabicyclo[3.2.0]heptan-3-yl]-1-phenoxypropane, m.p. 128°–130° C. (hydrochloride)
6. 2-[exo-6-p-Fluorophenyl-3-azabicyclo[3.2.0]heptan-3-yl]-1-p-fluorophenoxyethane, m.p. 177°–178° C. (hydrochloride)
7. 3-[exo-6-p-Fluorophenyl-3-azabicyclo[3.2.0]heptan-3-yl]-1-(1-naphthyloxy)propane
8. 3-[exo-6-p-Fluorophenyl-3-azabicyclo[3.2.0]heptan-3-yl]-1-p-t-butylphenoxypropane
9. 3-[exo-6-p-Fluorophenyl-3-azabicyclo[3.2.0]heptan-3-yl]-1-p-fluorophenoxypropane, m.p. 144°–146° C. (rosylate)

Example 10

N-(2-[exo-6-p-Fluorophenyl-3-azabicyclo[3.2.0]heptan-3-yl]-ethyl)thiobenzamide tosylate 2.4 g (7.1 mM) of N-(2-[exo-6-p-fluorophenyl-3-azabicyclo[3.2.0]heptan-3-yl]ethylbenzamide (DE 42 19 973) in 50 ml of toluene were mixed with 1.5 g (3.6 mM) of Lawesson's reagent and refluxed for 3 h with vigorous stirring. After cooling, the mixture was concentrated on a rotary evaporator, and the residue was partitioned between methylene chloride and water and rendered alkaline with 10% strength sodium hydroxide solution. The aqueous phase was reextracted twice with methylene chloride and the organic phase was then concentrated after drying with sodium sulfate. The crude product (3.5 g) was purified by column chromatography (silica gel, eluent methylene chloride/methanol 99:1). The purified free base was dissolved in 150 ml of ether and a solution of 1.0 g of p-toluenesulfonic acid in ethyl acetate was slowly added dropwise with ice-cooling and stirring. The precipitated salt was filtered off with suction under nitrogen, washed with ether and dried under nitrogen. 2.7 g (72%) of product were isolated as rosylate, m.p. 119°–122° C.

The following were prepared in a similar manner:
11. N-(2-[exo-6-p-Fluorophenyl-3-azabicyclo[3.2.0]heptan-3-yl]ethyl)-4-fluorothiobenzamide
12. N-(2-[exo-6-p-Fluorophenyl-3-azabicyclo[3.2.0]heptan-3-yl]ethyl)-4-chlorothiobenzamide Example 13

O-[exo-6-p-Fluorophenyl-3-azabicyclo[3.2.0]heptan-3-yl]-ethyl) benzoate maleate a) 20.0 g (142 mM) of benzoyl chloride and then additionally 14.4 g (142 mM) of triethylamine were added dropwise with vigorous stirring at room temperature to a solution of 11.5 g (142 mM) of chloroethanol in 200 ml of THF (exothermic reaction). After stirring for 1 h, the mixture was concentrated on a rotary evaporator, and the residue was partitioned between methylene chloride and water and acidified with 10% strength hydrochloric acid. The aqueous phase was reextracted twice with methylene chloride and the organic phase was then concentrated after drying with sodium sulfate. 26.0 g (99%) of 2-chloroethyl benzoate were isolated.

b) 3.0 g (15.7 mM) of exo-6-(p-fluorophenyl)-3-azabicyclo[3.2.0]heptane in 50 ml of toluene were mixed with 6.0 g (32 mM) of 2-chloroethyl benzoate and with 2.2 g (16 mM) of finely pulverized potassium carbonate in addition to 0.4 g of potassium iodide and refluxed for 15 h with vigorous stirring. After cooling, the mixture was concentrated on a rotary evaporator and the residue was partitioned between methylene chloride and water. The aqueous phase was reextracted twice with methylene chloride after adjusting to pH=10 and the organic phase was then concentrated after drying with sodium sulfate. The crude product (8.9 g) was purified by column chromatography (silica gel, eluent methylene chloride/methanol 99:1). The purified free base (2.8 g) was dissolved in 150 ml of ether and a solution of 1.0 g of maleic acid in 10 ml of acetone was slowly added dropwise with ice-cooling and stirring. The precipitated salt was filtered off with suction under nitrogen, washed with ether and dried under nitrogen. 3.9 g (53%) of product were isolated as the maleate, m.p. 139°–141° C.

The following can be prepared in a similar manner:
14. 2-[exo-6-p-Fluorophenyl-3-azabicyclo[3.2.0]heptan-3-yl]ethyl 4-fluorobenzoate Example 15

N-(2-[exo-6-p-Fluorophenyl-3-azabicyclo[3.2.0]heptan-3-yl]-ethyl)-1H-benzo[cd]indol-2-one 2.5 g (13.1 mM) of exo-6-p-fluorophenyl-3-azabicyclo[3.2.0]heptane in 50 ml of xylene were mixed with 3.0 g (13.1 mM) of 1-(2-chloroethyl)-1 H-benzo[cd]indol-2-one and with 1.9 g (13.1 mM) of finely pulverized potassium carbonate and 0.5 g of potassium iodide and refluxed for 3 h with vigorous stirring. After cooling, the mixture was concentrated on a rotary evaporator and the residue was partitioned between methylene chloride and water (pH=10). The aqueous phase was reextracted twice with methylene chloride and the organic phase was then concentrated after drying with sodium sulfate. The crude product (6.0 g) was purified by column chromatography (silica gel, eluent methylene chloride/methanol 98:2).

The free base (3.4 g) was dissolved in a little ethyl acetate and mixed with excess ethereal hydrochloric acid with ice-cooling. Precipitation was completed by addition of diethyl ether and the mixture was then stirred at 0° C. for 10 min. The precipitated hydrochloride was filtered off with suction under nitrogen, washed with diethyl ether and then dried at 40° C. in a vacuum drying oven. 2.7 g (49%) of pale powder were thus obtained, m.p.>250° C. (hydrochloride).

The following can be prepared in a similar manner:

16. N-(2-[exo-6-p-Chlorophenyl-3-azabicyclo[3.2.0]heptan-3-yl]ethyl)-1H-benzo[cd]indol-2-one, M.p. 233°–235° C. (hydrochloride)
17. N-(2-[exo-6-m-Fluorophenyl-3-azabicyclo[3.2.0]heptan-3-yl]ethyl)-1H-benzo[cd]indol-2-one
18. N-(2-[exo-6-m-Chlorophenyl-3-azabicyclo[3.2.0]heptan-3-yl]ethyl)-1H-benzo[cd]indol-2-one
19. 3,3-Dimethyl-1-(2-[exo-6-p-fluorophenyl-3-azabicyclo-[3.2.0]heptan-3-yl]ethyl)-2-indolinone, m.p. 198°–200° C. (hydrochloride)
20. 3,3-Dimethyl-1-(2-[exo-6-p-chlorophenyl-3-azabicyclo-[3.2.0]heptan-3-yl]ethyl)-2-indolinone, dec.p. 102° C. (maleate)
21. 3,3-Dimethyl-1-(2-[exo-6-m-chlorophenyl-3-azabicyclo-[3.2.0]heptan-3-yl]ethyl)-2-indolinone
22. 1-(2-[exo-6-p-Chlorophenyl-3-azabicyclo[3.2.0]heptan-3-yl]ethyl)-3,3,5-trimethyl-2-indolinone, m.p. 227°–229° C. (hydrochloride)
23. 3,4-Dichloro-N-(2-[exo-6-p-nitrophenyl-3-azabicyclo-[3.2.0]heptan-3-yl]ethyl)benzamide
24. 2,5-Difluoro-N-(2-[exo-6-p-fluorophenyl-3-azabicyclo-[3.2.0]heptan-3-yl]ethyl)benzamide
25. 2-Amino-N-(2-[exo-6-p-fluorophenyl-3-azabicyclo [3.2.0]-heptan-3-yl]ethyl)benzamide, m.p. 138°–139° C.
26. 2-Amino-N-(2-[exo-6-p-chlorophenyl-3-azabicyclo [3.2.0]-heptan-3-yl]ethyl)benzamide, m.p. 127°–128° C.
27. N-(2-[exo-6-p-Fluorophenyl-3-azabicyclo[3.2.0]heptan-3-yl]ethyl)-2-methylaminobenzamide, m.p. 105°–110° C. (dihydrochloride)
28. N-(2-[exo-6-p-Chlorophenyl-3-azabicyclo[3.2.0]heptan-3-yl]ethyl)-2-methylaminobenzamide, dec.p. 107° C. (dihydrochloride)
29. 3-Amino-N-(2-[exo-6-p-chlorophenyl-3-azabicyclo [3.2.0]-heptan-3-yl]ethyl)benzamide
30. 4-Amino-N-(2-[exo-6-p-chlorophenyl-3-azabicyclo [3.2.0]-heptan-3-yl]ethyl)benzamide
31. N-(2-[exo-6-p-Fluorophenyl-3-azabicyclo[3.2.0]heptan-3-yl]ethyl)thiophene-2-carboxamide, m.p. 185°–186° C. (hydrochloride)
32. 5-Chloro-N-(2-[exo-6-p-fluorophenyl-3-azabicyclo [3.2.0]-heptan-3-yl]ethyl)thiophene-2-carboxamide, m.p. 129°–131° C.
33. 5-Chloro-N-(2-[exo-6-p-chlorophenyl-3-azabicyclo [3.2.0]-heptan-3-yl]ethyl)thiophene-2-carboxamide, m.p. 136°–138° C.
34. 5-Chloro-N-(2-[exo-6-(5-chloro-2-thienyl)-3-azabicyclo-[3.2.0]heptan-3-yl]ethyl)thiophene-2-carboxamide
35. N-(2-[exo-6-p-Fluorophenyl-3-azabicyclo[3.2.0]heptan-3-yl]ethyl)benzo[b]furan-2-carboxamide, m.p. 250°–251° C. (hydrochloride)
36. 3-Chloro-N-(2-[exo-6-p-fluorophenyl-3-azabicyclo-[3.2.0]heptan-3-yl]ethyl)benzo[b]thiophene-2-carboxamide, m.p. 104°–106° C.
37. 3-Chloro-N-(2-[exo-6-p-chlorophenyl-3-azabicyclo [3.2.0]-heptan-3-yl]ethyl)benzo[b]thiophene-2-carboxamide
38. 3-Chloro-N-(2-[exo-6-p-nitrophenyl-3-azabicyclo [3.2.0]-heptan-3-yl]ethyl)benzo[b]thiophene-2-carboxamide
39. N-(2-[exo-6-p-Fluorophenyl-3-azabicyclo[3.2.0]heptan-3-yl]ethyl)inden-3-carboxamide, m.p. 107-109° C
40. N-(2-[exo-6-p-Chlorophenyl-3-azabicyclo[3.2.0]heptan-3-yl]ethyl)indene-3-carboxamide
41. N-(2-[exo-6-p-Fluorophenyl-3-azabicyclo[3.2.0]heptan-3-yl]ethyl)cyclopropanecarboxamide, m.p. 104°–105° C.
42. N-(2-[exo-6-p-Fluorophenyl-3-azabicyclo[3.2.0]heptan-3-yl]ethyl)cyclopentanecarboxamide, m.p. 78°–82° C.
43. N-(2-[exo-6-p-Chlorophenyl-3-azabicyclo[3.2.0]heptan-3-yl]ethyl)cyclopentanecarboxamide
44. N-(2-[exo-6-p-Fluorophenyl-3-azabicyclo[3.2.0]heptan-3-yl]ethyl)cyclohexanecarboxamide, m.p. 111°–113° C.
45. N-(2-[exo-6-p-Chlorophenyl-3-azabicyclo[3.2.0]heptan-3-yl]ethyl)cyclohexanecarboxamide, m.p. 106°–107° C.
46. N-(2-[exo-6-p-Fluorophenyl-3-azabicyclo[3.2.0]heptan-3-yl]ethyl)naphthalene-l-carboxamide, m.p. 202°–204° C. (hydrochloride)
47. N-(2-[exo-6-p-Fluorophenyl-3-azabicyclo[3.2.0]heptan-3-yl]ethyl)indole-2-carboxamide
48. N-(2-[exo-6-p-Chlorophenyl-3-azabicyclo[3.2.0]heptan-3-yl]ethyl)indole-3-carboxamide Example 49 exo-6-p-Fluorophenyl-3-[2-(1-naphthyl)ethyl]-3-azabicyclo[3.2.0]heptane 2.5 g (13.1 mM) of exo-6-p-fluorophenyl-3-azabicyclo-[3.2.0]heptane in 50 ml of xylene were mixed with 3.2 g (13.6 mM) of 1-(2-bromoethyl)naphthalene and with 1.9 g (13.1 mM) of finely pulverized potassium carbonate and 0.5 g of potassium iodide and refluxed for 2 h with vigorous stirring. After cooling, the mixture was concentrated on a rotary evaporator and the residue was partitioned between methylene chloride and water (pH=10). The aqueous phase was reextracted twice and methylene chloride and the organic phase was then concentrated after drying with sodium sulfate. The crude product (6.7 g) was purified by column chromatography (silica gel, eluent methylene chloride/methanol 97.5:2.5).

The free base (3.3 g) was dissolved in diethyl ether and a little ethyl acetate and mixed with excess ethereal hydrochloric acid with ice-cooling. The precipitated hydrochloride was filtered off with suction under nitrogen, washed with diethyl ether and then dried at 40° C. in a vacuum drying oven. 1.2 g (24%) of white, fine powder were thus obtained, m.p. 212°–214° C. (hydrochloride).

The following can be prepared in a similar manner:
50. exo-6-p-Chlorophenyl-3-[2-(1-naphthyl)ethyl]-3-azabicyclo[3.2.0]heptane, m.p. 215°–216° C. (hydrochloride)
51. exo-6-m-Chlorophenyl-3-[2-(1-naphthyl)ethyl]-3-azabicyclo[3.2.0]heptane, m.p. 185°–187° C. (hydrochloride)
52. exo-6-(5-Chloro-2-thienyl)-3-[2-(1-naphthyl)ethyl]-3-azabicyclo[3.2.0]heptane, m.p. 209°–210° C. (hydrochloride)
53. exo-6-p-Fluorophenyl-3-[2-(2-naphthyl)ethyl]-3-azabicyclo[3.2.0]heptane, m.p. 163°–164° C. (hydrochloride)
54. exo-6-p-Fluorophenyl-3-[1-naphthylmethyl]-3-azabicyclo-[3.2.0]heptane, m.p. 114°–116° C. (maleate)
55. exo-6-p-Fluorophenyl-3-[2-naphthylmethyl]-3-azabicyclo-[3.2.0]heptane, m.p. 153°–155° C. (hydrochloride)
56. 4-(6-p-Fluorophenyl-3-azabicyclo[3.2.0]heptan-3-yl)-1-(thiophen-2-yl)butan-1-one, m.p. 197°–199° C. (hydrochloride)
57. 4-(6-p-Chlorophenyl-3-azabicyclo[3.2.0]heptan-3-yl)-1-(thiophen-2-yl)butan-1-one, m.p. 176°–177° C. (hydrochloride)

Example 58

N-(2-[exo-6-p-Fluorophenyl-3-azabicyclo[3.2.0]heptan-3-yl]-ethyl)-4-phenyl-2-pyrrolidinone tartrate a) 25.0 g (131 mM) of exo-6-(p-fluorophenyl)-3-azabicyclo[3.2.0]heptane in 350 ml of THF were mixed with 74.0 g (523 mM) of 1-bromo-2-chloroethane and with 18.0 g (131 mM) of finely pulverized potassium carbonate and refluxed for 15 h with vigorous stirring. After cooling, the mixture was concentrated on a rotary evaporator and the residue was partitioned between methyl t-butyl ether and water.

After adjusting to pH=10, the aqueous phase was reextracted twice with methyl t-butyl ether and the organic phase was then concentrated after drying with sodium sulfate. The crude product (34.8 g) was purified by column chromatography (silica gel, eluent methylene chloride). 21.9 g (66%) of 3-(β-chloroethyl)-exo-6-(p-fluorophenyl)-3-azabicyclo[3.2.0]heptane were isolated as a pale yellow oil.

b) 0.30 g (9.9 mM) of 80% strength sodium hydride was introduced at room temperature under nitrogen into 1.56 g (9.9 mM) of 4-phenyl-2-pyrrolidinone in 30 ml of DMF and the mixture was heated at 120° C. for 1 h with vigorous stirring. After cooling, 2.5 g (9.9 mM) of 3-(β-chloroethyl)-exo-6-(p-fluorophenyl)-3-azabicyclo[3.2.0]heptane were added and the mixture was stirred for a further 2 h at a bath temperature of 140° C. After cooling, the mixture was concentrated on a rotary evaporator and the residue was partitioned between methyl t-butyl ether and water. After adjusting to pH=10, the aqueous phase was reextracted twice with methyl t-butyl ether and the organic phase was then concentrated after drying with sodium sulfate. The crude product (3.5 g) was purified by column chromatography (silica gel, eluent methylene chloride/methanol 97:3). The purified free base (2.5 g) was dissolved in 150 ml of ether and a solution of 1.0 g of tartaric acid in 10 ml of ethanol was slowly added dropwise with ice-cooling and stirring. The precipitated salt was filtered off with suction under nitrogen, washed with ether and dried under nitrogen. 3.2 g (61%) of product were isolated as the tartrate, m.p. 74°–77° C.

Example 59

N-(2-[exo-6-p-Fluorophenyl-3-azabicyclo[3.2.0] heptan-3-yl]-ethyl)-2-benzoxazolinone a) 10 g (74 mM) of 2-benzoxazolinone in 150 ml of 1,2-dichloroethane were mixed with 7.1 g (111 mM) of potassium hydroxide powder (88%) and 0.5 g of benzyltriethylammonium chloride (TEBAC) and refluxed for 4 h with vigorous stirring. After cooling, the mixture was concentrated on a rotary evaporator and the residue was partitioned between methylene chloride and water.

The aqueous phase was reextracted twice with methylene chloride and the organic phase was then concentrated after drying with sodium sulfate. The crude product (11.7 g) was purified by column chromatography (silica gel, eluent methylene chloride). 8.2 g (56%) of N-(2-chloro)ethyl-2-benzoxazolinone were isolated.

b) 2.5 g (13.1 mM) of exo-6-(p-fluorophenyl)-3-azabicyclo[3.2.0]heptane in 40 ml of xylene were mixed with 3.0 g (15.2 mM) of N-(2-chloro)ethyl-2-benzoxazolinone and with 1.8 g (13.1 mM) of finely pulverized potassium carbonate in addition to 0.3 g of potassium iodide and refluxed for 7 h with vigorous stirring. After cooling, the mixture was concentrated on a rotary evaporator and the residue was partitioned between methylene chloride and water.

After adjusting to pH=9, the aqueous phase was reextracted twice with methylene chloride and the organic phase was then concentrated after drying with sodium sulfate. The crude product (6.5 g) was purified by column chromatography (silica gel, eluent methylene chloride/-methanol 98:2).

3.5 g (76%) of product were isolated, m.p. 138°–140° C. (fumarate).

Example 60

N-(2-[exo-6-p-Fluorophenyl-3-azabicyclo[3.2.0] heptan-3-yl]-ethyl)isoindolinone a) 13.3 g (100 mM) of phthalimidine in 200 ml of 1,2-dichloroethane were mixed with 9.6 g (150 mM) of potassium hydroxide powder (88 %) and 0.5 g of benzyltriethylammonium chloride (TEBAC) and refluxed for 5 h with vigorous stirring. After cooling, the mixture was concentrated on a rotary evaporator and the residue was partitioned between methylene chloride and water.

After adjusting to pH=6, the aqueous phase was reextracted twice with methylene chloride and the organic phase was then concentrated after drying with sodium sulfate. The crude product (15.0 g) was purified by column chromatography (silica gel, eluent methylene chloride/methanol 97:3). 9.8 g (50%) of N-(2-chloro)-ethylisoindolinone were isolated.

b) 2.5 g (13.1 mM) of exo-6-(p-fluorophenyl)-3-azabicyclo[3.2.0]heptane in 50 ml of xylene were mixed with 2.75 g (14.0 mM) of N-(2-chloro)ethylisoindolinone and with 2.0 g (14.0 mM) of finely pulverized potassium carbonate in addition to 0.5 g of potassium iodide and refluxed for 8 h with vigorous stirring. After cooling, the mixture was concentrated on a rotary evaporator and the residue was partitioned between methylene chloride and water.

After adjusting to pH=10, the aqueous phase was reextracted with methylene chloride and the organic phase was then concentrated after drying with sodium sulfate. The crude product (5.6 g) was purified by column chromatography (silica gel, eluent methylene chloride/methanol 96:4). 3.5 g (76%) of product were isolated, m.p. 223°–225° C. (hydrochloride).

The following were prepared in a similar manner to Example 60:

61. 1-(2-[exo-6-p-Fluorophenyl-3-azabicyclo[3.2.0]heptan-3-yl]ethyl)indazole, m.p. 164°–166° C. (hyrochloride)
62. 1-(2-[exo-6-p-Fluorophenyl-3-azabicyclo[3.2.0]heptan-3-yl]ethyl)-1,8-naphthalene sultam, m.p. 206°–208° C. (hydrochloride)
63. 4-(2-[exo-6-p-Fluorophenyl-3-azabicyclo[3.2.0]heptan-3-yl]ethyl)-1,4-benzoxazin-3-one, m.p. 166°–168° C. (tosylate)
64. 1-(2-[exo-6-p-Fluorophenyl-3-azabicyclo[3.2.0]heptan-3-yl]ethyl)quinoxalin-2(1H)-one, m.p. 54°–56° C. (tartrate)

Example 65

1-(2-[exo-6-p-Fluorophenyl-3-azabicyclo[3.2.0]heptan-3-yl]-ethyl)-2-indolinone a) 13.3 g (100 mM) of oxindole in 150 ml of 1,2-dichloroethane were mixed with 11.0 g (173 mM) of potassium hydroxide powder (88%) and 0.5 g of benzyltriethylammonium chloride (TEBAC) and refluxed for 6 h with vigorous stirring. After cooling, the mixture was concentrated on a rotary evaporator and the residue was partitioned between methylene chloride and water.

The aqueous phase was reextracted twice with methylene chloride and the organic phase was then concentrated after drying with sodium sulfate. The crude product (15.5) g was purified by column chromatography (silica gel, eluent methylene chloride/methanol 99:1). 7.1 g of a mixture of N-(2-chloro)ethyloxindole and the corresponding spirocyclopropyl derivative were isolated.

b) 3.4 g (17.8 mM) of exo-6-(p-fluorophenyl)-3-azabicyclo-[3.2.0]heptane in 50 ml of xylene were mixed with 5.2 g of the above product mixture and with 3.3 g (24.0 mM) of finely pulverized potassium carbonate in addition to 0.5 g of potassium iodide and refluxed for 9 h with vigorous stirring. After cooling, the mixture was concentrated on a rotary evaporator and the residue was partitioned between methylene chloride and water.

After adjusting to pH=10, the aqueous phase was reextracted twice with methylene chloride and the organic phase was then concentrated after drying with sodium sulfate. The crude product (8.4 g) was purified by column chromatography (silica gel, eluent methylene chloride/methanol 99:1). 3.5 g of a product mixture (1:1) were isolated, which was again subjected to the fine separation of column chromatography (silica gel, eluent n-hexane/ethyl acetate 1:1).

1.9 g (31%) of 1-(2-[exo-6-p-fluorophenyl-3-azabicyclo[3.2.0]heptan-3-yl]ethyl)-2-indolinone were isolated as a polar substance, m.p. 91°–93° C. (tartrate).

Example 66

1-(2-[exo-6-p-Fluorophenyl-3-azabicyclo[3.2.0]heptan-3-yl]ethyl)spiro[cyclopropane-1',3-indolin-2-one]

1.4 g (21%) of 1-(2-[exo-6-p-fluorophenyl-3-azabicyclo[3.2.0]heptan-3-yl]ethyl)spiro[cyclopropane-1', 3-indolin-2-one], which decomposed from 129° C. after conversion to the tartrate salt, were isolated as a non-polar component of the product mixture from Example 65b.

Example 67

5-(2-[exo-6-p-Fluorophenyl-3-azabicyclo[3.2.0]heptan-3-yl]-ethyl)-2-phenylamino-3,6-dimethyl-4(3H)-pyrimidinone 3.0 g (15.7 mM) of exo-6-p-fluorophenyl-7-methyl-1,5-cis-3,7-diazabicyclo[3.3.0]octane in 60 ml of xylene were mixed with 4.4 g (15.7 mM) of 5β-chloroethyl-2-phenylamino-3,6-dimethyl-4(3H)-pyrimidinone (prepared from phenylguanidine and α-acetyl-γ-butyrolactone corresponding to the syntheses in EP 110 435) and with 2.2 g (15.7 mM) of finely pulverized potassium carbonate and 0.4 g of potassium iodide and refluxed for 10 h with vigorous stirring.

After cooling, the mixture was concentrated on a rotary evaporator and the residue was partitioned between methylene chloride and water (pH=10, filtration of the insoluble flocks with suction). The aqueous phase was reextracted twice with methylene chloride and the organic phase was then concentrated after drying with sodium sulfate. The crude product (8.2 g) was purified by column chromatography (silica gel, eluent methylene chloride/methanol 93:7). 5.3 g (78%) of product of m.p. 61°–63° C. were isolated.

The following can be prepared in a similar manner:
68. 5-(2-[exo-6-p-Fluorophenyl-3-azabicyclo[3.2.0]heptan-3-yl]ethyl)-2-benzylamino-3,6-dimethyl-4(3H)-pyrimidinone, m.p. 144°–146° C. (dihydrochloride)
69. 5-(2-[exo-6-p-Fluorophenyl-3-azabicyclo[3.2.0]heptan-3-yl]ethyl)-2-cyanoamino-3,6-dimethyl-4(3H)-pyrimidinone
70. 5-(2-[exo-6-p-Chlorophenyl-3-azabicyclo[3.2.0]heptan-3-yl]ethyl)-2-phenylamino-3,6-dimethyl-4(3H)-pyrimidinone
71. 5-(2-[exo-6-m-Chlorophenyl-3-azabicyclo[3.2.0]heptan-3-yl]ethyl)-2-phenylamino-3,6-dimethyl-4(3H)-pyrimidinone
72. 5-(2-[exo-6-(5-Chlorothien-2-yl)-3-azabicyclo[3.2.0]-heptan-3-yl]ethyl)-2-phenylamino-3,6-dimethyl-4(3H)-pyrimidinone
73. 5-(2-[exo-6-Thien-3-yl-3-azabicyclo[3.2.0]-heptan-3-yl]ethyl)-2-phenylamino-3,6-dimethyl-4(3H)-pyrimidinone Example 74

5-(2-[exo-6-p-Fluorophenyl-3-azabicyclo[3.2.0]heptan-3-yl]-ethyl)-2-(N-methyl-N-phenyl)amino-3,6-dimethyl-4(3H)-pyrimidinone 2.9 g (6.7 mM) of 5-(2-[exo-6-p-fluorophenyl-3-azabicyclo-[3.2.0]heptan-3-yl]ethyl)-2-phenylamino-3,6-dimethyl-4(3H)-pyrimidinone in 30 ml of DMF were mixed in portions with 0.21 g (7.0 mM) of sodium hydride (80%) with vigorous stirring (exothermic reaction). The mixture was stirred at 70° C. for a further 0.3 h and 1.0 g (7.0 mM) of methyl iodide was then added. The reaction mixture was stirred at 90° C. for 2 h and then concentrated in vacuo. The residue was partitioned between water and methyl t-butyl ether (pH=10) and the aqueous phase was reextracted twice with methyl t-butyl ether. Drying and concentration of the organic phases afforded 1.2 g (40%) of product, m.p. 115°–117° C. (hydrochloride×2H$_2$O).

We claim:
1. An N-substituted 3-azabicyclo[3.2.0]heptane derivative of the formula I

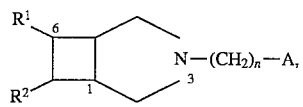

I where

R$^1$ is a phenyl or thienyl group which is unsubstituted or mono- or disubstituted by halogen atoms or C$_1$–C$_4$-alkyl, trifluoromethyl, hydroxyl, C$_1$–C$_4$-alkoxy, amino, mono-methylamino, dimethylamino, cyano or nitro groups, R$^2$ is a hydrogen atom or a phenyl group which is unsubstituted or substituted by halogen, methoxy, hydroxyl or amino, n is the number 1, 2, 3 or 4, A is a hydrogen atom or one of the radicals

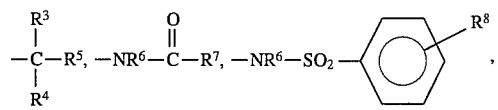

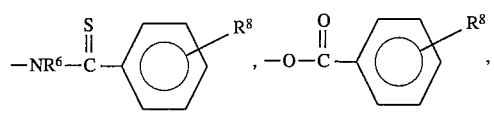

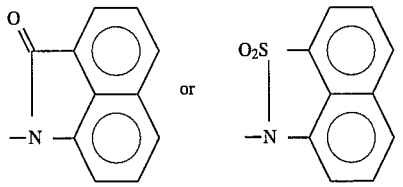

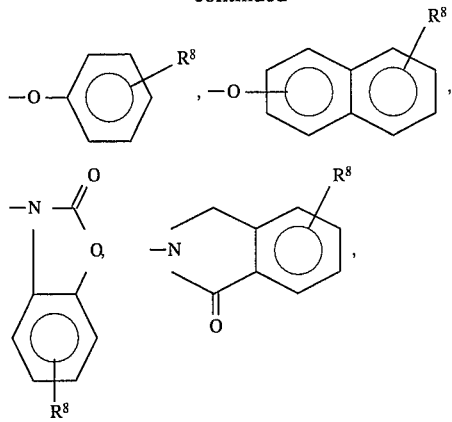

$R^3$ is a hydrogen atom or a hydroxyl radical, $R^4$ is a hydrogen atom or $R^3$ and $R^4$ together are an oxygen atom, $R^5$ is a thienyl or naphthyl group which is unsubstituted or substituted by fluorine or chlorine, $R^6$ is a hydrogen atom or a methyl group, $R^7$ is a phenyl group which is disubstituted by fluorine, chlorine, hydroxyl or methoxy or monosubstituted by amino, $C_{1-4}$-alkylamino or di-$C_{1-4}$-alkylamino or a thienyl, naphthyl, benzofuryl, benzothienyl, indolyl, N-methylindolyl or indenyl group which is unsubstituted or substituted by fluorine, chlorine or nitro or a $C_3$- to $C_6$-cycloalkyl group, $R^8$ is hydrogen, fluorine, chlorine, $C_{1-4}$-alkyl, methoxy or amino, $R^9$ is hydrogen or a methyl group and $R^{10}$ is hydrogen or a methyl group or $R^9$ and $R^{10}$, together with the ring C atom, are a spiro-cyclopropane ring, $R^{11}$ is a phenyl or benzyl radical which is unsubstituted or substituted by fluorine or chlorine, or a cyano group, and their salts with physiologically tolerable acids.

2. An N-substituted 3-azabicyclo[3.2.0]heptane derivative of the formula I as claimed in claim 1 for use in the control of diseases.

* * * * *